United States Patent
Daum

(10) Patent No.: US 7,286,877 B2
(45) Date of Patent: *Oct. 23, 2007

(54) DEVICE PROGRAMMER WITH ENCLOSED IMAGING CAPABILITY

(75) Inventor: Douglas Daum, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 416 days.

This patent is subject to a terminal disclaimer.

(21) Appl. No.: 10/792,562

(22) Filed: Mar. 3, 2004

(65) Prior Publication Data

US 2004/0230248 A1 Nov. 18, 2004

Related U.S. Application Data

(63) Continuation-in-part of application No. 09/905,562, filed on Jul. 13, 2001, now Pat. No. 6,704,600.

(51) Int. Cl.
*A61N 1/372* (2006.01)
*A61B 8/00* (2006.01)
*A61B 5/05* (2006.01)

(52) U.S. Cl. .................... 607/30; 600/407; 600/508
(58) Field of Classification Search .................... None
See application file for complete search history.

(56) References Cited

U.S. PATENT DOCUMENTS

| | | | |
|---|---|---|---|
| 4,481,950 A | 11/1984 | Duggan | |
| 4,936,304 A * | 6/1990 | Kresh et al. | 607/23 |
| 5,113,859 A | 5/1992 | Funke | |
| 5,139,020 A | 8/1992 | Koestner et al. | |
| 5,188,106 A | 2/1993 | Nappholz et al. | |
| 5,191,885 A | 3/1993 | Bilof et al. | |
| 5,524,624 A * | 6/1996 | Tepper et al. | 600/439 |
| 5,609,629 A | 3/1997 | Fearnot et al. | |
| 5,713,937 A | 2/1998 | Nappholz et al. | |
| 5,727,552 A | 3/1998 | Ryan | |
| 5,749,833 A | 5/1998 | Hakki et al. | |
| 5,824,049 A | 10/1998 | Ragheb et al. | |

(Continued)

OTHER PUBLICATIONS

SonoSite 180 and Sono Heart Systems "Imagine Ultrasound at Every Point of Care": www.sonosite.com, 2001.

(Continued)

*Primary Examiner*—Kristen Droesch Mullen
(74) *Attorney, Agent, or Firm*—Schwegman, Lundberg & Woessner P.A.

(57) ABSTRACT

Methods and electronic tools for imaging a chest region of a patient and communicating with a heart stimulation device used by the patient are disclosed. The electronic tool may include a communications device for two-way data transmission of signals encoded with information to and from the heart stimulation device. The tool may also include an imaging device for radiating energy onto the chest of the patient and receiving energy as it is reflected from the chest region to produce an image signal. The tool may include a display screen for showing an image of the chest area and/or the information received from the heart stimulation device. The tool may also include a processor for formulating and/or analyzing information sent to and/or received from the heart stimulation device. One method of using the electronic tool includes analyzing the image signal and/or received information to provide instructions to the heart stimulation device.

31 Claims, 6 Drawing Sheets

U.S. PATENT DOCUMENTS

| | | |
|---|---|---|
| 5,859,922 A | 1/1999 | Hoffmann |
| 5,861,018 A | 1/1999 | Feierbach |
| 5,891,178 A | 4/1999 | Mann et al. |
| 5,921,933 A | 7/1999 | Sarkis et al. |
| 6,298,257 B1 | 10/2001 | Hall et al. |
| 6,305,381 B1 | 10/2001 | Weijand et al. |
| 6,308,715 B1 | 10/2001 | Weissman et al. |
| 6,345,200 B1 | 2/2002 | Mouchawar et al. |
| 6,496,715 B1 | 12/2002 | Lee et al. |

OTHER PUBLICATIONS

SonoSite "Personal Cardiac Imaging", personal hand carried ultrasound device; www.sonosite.com, 2000.

* cited by examiner

DEVICE PROGRAMMER WITH ENCLOSED IMAGING CAPABILITY

RELATED APPLICATION

This application is a continuation-in-part and claims priority of invention under 35 U.S.C. §120 from U.S. application Ser. No. 09/905,562, filed Jul. 13, 2001, now U.S. Pat. No. 6,704,600 which is incorporated herein by reference.

TECHNICAL FIELD

The present invention is directed to imaging systems and programmers for cardiac devices. More particularly, the present invention is directed to the combination of device programmers with imaging systems.

BACKGROUND

Cardiac devices, such as pacemakers and implantable cardiac defibrillators, have electrical leads that must be implanted within or onto the surface of the heart. The electrical leads may be used to detect electrical events occurring in the heart and to pass an electrical signal caused by the electrical event to the cardiac device. The electrical leads may also be used to provide electrical stimulation from the cardiac device to the heart tissue. The electrical stimulation causes contraction of the heart tissue. For example, electrical stimulation can be provided to the heart to vary the delay between the depolarization of the atrial area and depolarization of the ventricle area.

To properly install the electrical leads of the cardiac device, sophisticated imaging systems such as fluoroscopy are typically used to provide a high resolution X-ray of the patient's chest as the leads are being inserted. Generally, the sophisticated imaging systems are permanently located in electrophysiology or surgical rooms, and implantation of the device must occur at these locations.

In addition to the sophisticated imaging system, the physician employs a device programmer to adjust performance parameters of the implantable device. The programmer generally uses telemetry to send and receive signals, such as magnetic waves, to and from the implantable device. Thus, the physician uses the imaging system to view and position the electrical leads and to view the hemodynamic response of the heart. While viewing the leads and response, the physician also adjusts the operational parameters of the device with the programmer to alter the hemodynamic response.

Therefore, there is a need for a tool that allows installation of the leads in a less rigorous medical environment while simplifying the evaluation and optimization of device performance.

SUMMARY

The present invention addresses problems such as but not limited to those mentioned above by providing an electronic tool having a programmer system and an imaging system. A device programmer is typically portable and by combining an imaging system such as ultrasound with the programmer in the electronic tool, the implantation process may be performed in environments other than surgical labs. Furthermore, the tool provides a display that may show an image of the patient's heart including the electrical leads while simultaneously showing ordinary programmer information such as electrogram signals received from the implantable device. The tool may also provide a processor to analyze the image for lead position and hemodynamic response and may also analyze the electrogram signals. From this analysis, the tool may communicate signals to alter the device parameters and improve hemodynamic response.

The present invention may be viewed as an electronic tool for communicating with a heart stimulation device and for imaging a chest region of a patient. The tool includes an enclosure and an imaging device at least partially disposed within the enclosure. The imaging device radiates energy onto the chest region and detects energy reflected by the chest region to produce an image signal. The tool also includes a communication device at least partially disposed within the enclosure that sends to or receives from the heart stimulation device a first signal with encoded information.

The invention may be viewed as another electronic tool for communicating with a heart stimulation device and for imaging a chest region of a patient. The electronic tool includes an imaging device that radiates energy onto the chest region and that detects energy reflected by the chest region to produce an image signal. The tool includes a communication device that sends to or receives from the heart stimulation device a first signal with encoded information. At least one display screen is in electrical communication with the imaging device and the communication device, and the display screen displays a representation of the image signal or displays information from the first signal sent from or received by the communication device.

The present invention may be viewed as another electronic tool for communicating with a heart stimulation device and for imaging a chest region of a patient. The electronic tool includes an imaging device that radiates energy onto the chest region and that detects energy reflected by the chest region to produce an image signal. The tool includes a communication device that receives a first signal with encoded information from the heart stimulation device. At least one processing device is in electrical communication with the imaging device or the communication device, wherein the at least one processing device analyzes the image signal or analyzes the information encoded on the first signal to formulate an instruction for the heart stimulation device.

The present invention may be viewed as another electronic tool for communicating with a heart stimulation device and for imaging a chest region of a patient. The tool includes means for radiating energy onto the chest region and for detecting energy reflected by the chest region to produce an image signal. The tool includes means for radiating a first signal with encoded information onto the heart stimulation device. The tool also includes means for formulating the first signal based at least on the image signal.

The present invention may be viewed as a method of programming a heart stimulation device having one or more electrical leads placed in a heart of a patient. The method involves radiating energy onto an area around the heart of the patient and receiving energy reflected by the one or more electrical leads positioned in the heart. The method further involves producing an image signal representative of the received energy and analyzing, with a processing device, the image signal to measure motion of the electrical lead. The method also involves producing, with the processing device and in response to the measured motion of the electrical lead, a signal encoding instructions for varying stimulation one or more stimulation parameters of the heart stimulation device.

The present invention may be viewed as a method for positioning an electrical lead of a heart stimulation device in a heart of a patient. The method involves radiating, with an imaging device at least partially within a first enclosure, energy onto an area around the heart of the patient and receiving energy reflected by the electrical lead positioned in the heart. The method further involves producing an image signal representative of the received energy and involves receiving, with a communications device at least partially within the first enclosure, an activity signal radiated from the heart stimulation device. The method also involves displaying, on a display screen, a first representation of the image signal and a second representation of the activity signal.

The present invention may be viewed as an electronic tool for communicating with a heart stimulation device and for imaging a chest region of a patient. The electronic tool includes an imaging device that radiates energy onto the chest region and that detects energy reflected by the chest region to produce an image signal. The tool includes a communication device that radiates a first signal with encoded information to the heart stimulation device. The tool also includes at least one processing device in electrical communication with the imaging device and the communication device, wherein the at least one processing device analyzes the image signal to formulate an instruction for the heart stimulation device that is encoded onto the first signal.

The present invention may be viewed as a method of programming a heart stimulation device of a patient. The method involves radiating, with an imaging device, energy onto an area around the heart of the patient and involves receiving, with the imaging device, energy reflected by the area around the heart. The method also involves producing, with the imaging device, an image signal representative of the received energy, and involves receiving a first signal radiated by the heart stimulation device. The method further involves analyzing, with a processing device in electrical communication with the imaging device and the communications device, the first signal to measure a response of the heart. Additionally, the method involves producing, with the processing device and in response to the measured response, a second signal encoding instructions for varying one or more stimulation parameters of the heart stimulation device.

DETAILED DESCRIPTION

Figure 1:
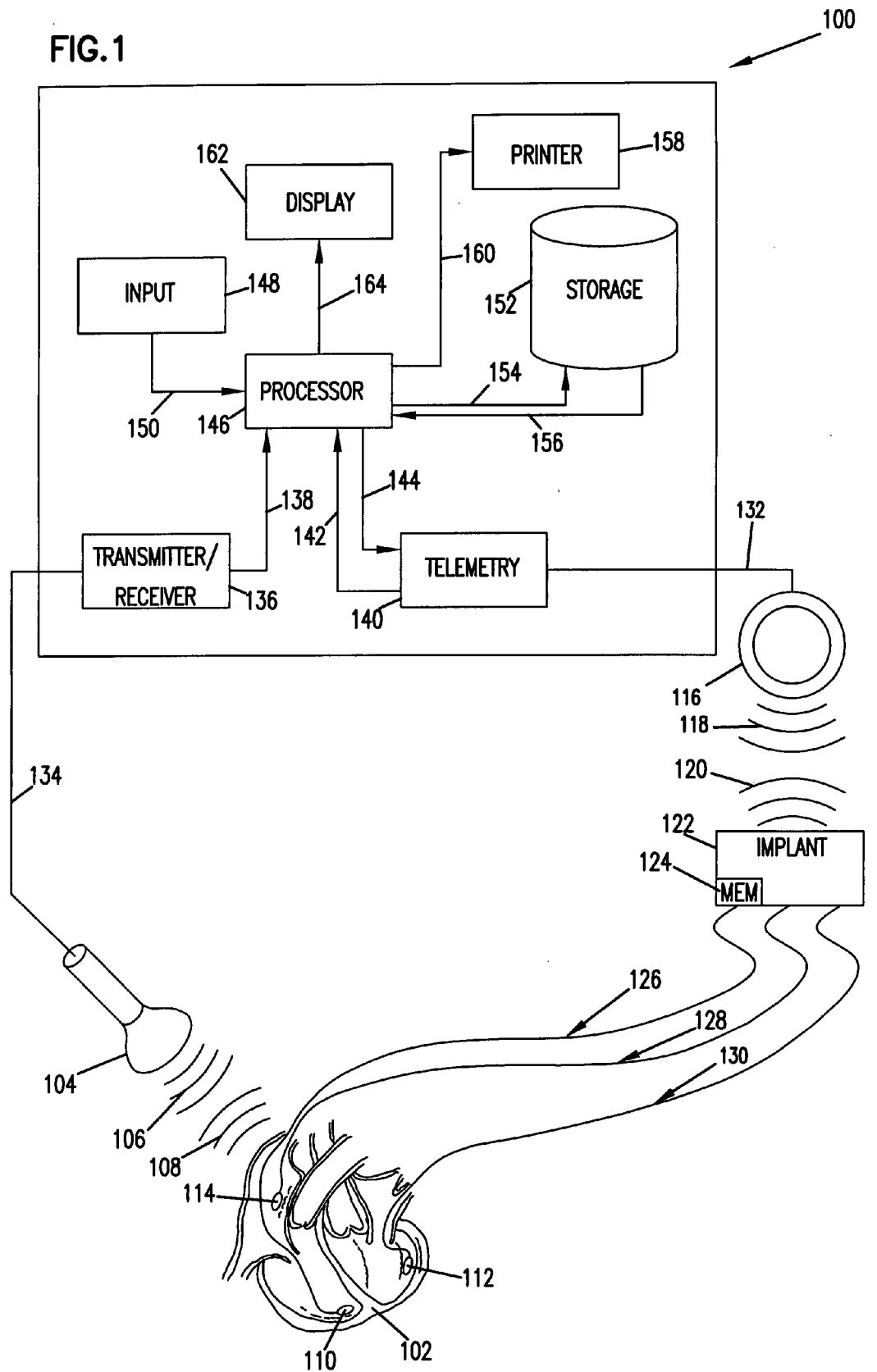
FIG. 1 illustrates a block diagram of the components of one embodiment of the present invention.

Various embodiments of the present invention will be described in detail with reference to the drawings, wherein like reference numerals represent like parts and assemblies through the several views. Reference to various embodiments does not limit the scope of the invention, which is limited only by the scope of the claims attached hereto.

Embodiments of the present invention include an electronic tool for application to various activities such as electrical lead placement and implantable device optimization. Providing an imaging system with a device communication system allows a single tool to obtain images of the lead position and the hemodynamic response as well as obtain data signals indicative of the hemodynamic response while also communicating instructions to the implantable device to control its operation. A processing system may be included within the tool to facilitate automatic analysis and corresponding parameter optimization. A display may be included to facilitate user visualization of the lead position and/or hemodynamic response. Including an input device within the tool allows the user to influence the instructions communicated to the implantable device.

FIG. 1 shows a block diagram of an exemplary electronic tool 100 incorporating programming and imaging functions. The tool 100 in this example includes an imaging device such as an ultrasound transmitter/receiver module 136 that sends and receives electrical signals through line 134 to a phased array transducer 104. The phased array transducer 104 generates ultrasound energy waves 106 that radiate onto the chest of the patient having an implantable device 122. The heart 102 of the patient may have several electrodes installed including an atrial electrode 114, a right ventricle electrode 110, and a left ventricle electrode 112. These electrodes are electrically connected to the implantable device 122 through leads 126, 128, and 130. For embodiments where an ultrasound imaging device 136 is used, the leads 126, 128, and 130 and the electrodes 110, 112, and 114 may be coated with an echogenic material that is opaque to ultrasound energy. The ultrasound imaging device may employ circuitry such as that known in the art for ultrasound imaging.

The transmitter/receiver module 136 is in electrical communication with a processor 146 through line 138. The transmitter/receiver module 136 passes an image signal created from the reception of ultrasound energy by the phased transducer array 104 to the processor 146. The image signal may contain digital data created by an analog-to-digital conversion implemented by the transmitter/receiver module 136. The processor 146 may then employ image processing techniques to the image signal data to analyze various aspects of the signal, as is discussed below. Alternatively, or in addition to feeding the image signal to the processor 146, the transmitter/receiver module 136 may feed the image signal directly to a display device 162 for real-time display of a representation of the image signal.

The electronic tool 100 also includes a communications device such as a telemetry module 140. Telemetry module 140 receives signals from the processor 146 through line 144 and provides signals to the processor through line 142. Telemetry module 140 sends and receives signals from a loop antenna 116, which typically is a wire loop. The loop antenna 116 radiates electromagnetic energy in the form of a signal 118. The signal 118 generally has encoded information such as instructions for the implantable device 122 or trending data to be stored by the implantable device 122. The telemetry communications device 140 may use circuitry such as that known in the art for implantable device communications.

The implantable device 122 receives the signal 118 from the loop antenna 116 and includes its own processing device for interpreting the encoded information and carrying out the instruction. Typically, the instruction involves adjusting the timing of the stimulation pulse provided to one of the electrodes in the heart 102. The implantable device 122 generally includes memory 124 such as for storing instructions received from the loop antenna 116. The memory 124 may also store trending information, such as electrogram information that is recorded by the implantable device 122 through the detection of electrical events by the electrodes 110, 112, and 114 in the heart 102. Other trending information that may be stored by memory 124 includes but is not limited to heart size and left ventricle septum-lateral wall synchronization.

The implantable device 122 radiates a signal 120 that also has encoded information, such as electrogram data being measured in real-time by the electrodes 110, 112, and 114 or trending data that is stored by memory 124. The radiated signal 120 is received by the loop antenna 116 and is converted to an electrical signal that is transferred to the telemetry module 140. The telemetry module 140 may then employ an analog-to-digital conversion to convert the received signal to a data signal that is then passed to the processor 146. Alternatively, or in addition to feeding received signals to the processor 146, the telemetry module 140 may feed signals directly to the display device 162 for real-time display of the information encoded on the signal 120.

In an alternative embodiment, antenna 116 is of a type optimally configured for transmitting and receiving RF signals. The RF antenna radiates electromagnetic energy in the form of an RF signal 118. The signal 118 generally has encoded information such as instructions for the implantable device 122 or trending data to be stored by the implantable device 122. In an embodiment utilizing RF data signals, the telemetry communications device 140 may use basic RF base station circuitry such as that known in the art for a basic RF system.

The implantable device 122, which also includes RF circuitry that allows the implantable device 122 to perform as a mobile RF terminal, has a communications link with the telemetry communications device 140 via antenna 116. The implantable device 122 receives the signal 118 from the antenna 116 and includes its own processing device for interpreting the encoded information and carrying out the instruction.

RF technology provides for wireless transmission of data by digital radio signals at a particular frequency. It provides a means for maintaining bi-directional or two-way, online radio connection between the telemetry communications device 140 and the implantable device 122.

The processor 146 may employ various operations, discussed in more detail below with reference to FIGS. 3, 4, and 5 to utilize the signals received from the imaging device 136 and/or the communications device 140. The processor 146 may store data to and access data from storage device 152, such as electronic memory or magnetic storage. Data is transferred to the storage device 152 through line 154, and data is received from the storage device 152 through line 156. The processor 146 may be a general-purpose computer processor or processor typically used for a programmer. Furthermore as mentioned below, the processor 146, in addition to being a general-purpose programmable processor, may be firmware, hard-wired logic, analog circuitry, other special purpose circuitry, or any combination thereof.

The processor 146 may also transfer a display signal to a display device 162 through line 164. The display signal may include the image signal produced by the imaging device 136 as well as an information signal produced by communication device 140. The image signal component from the imaging device 136 is typically an ultrasound image. The information signal component from the communications device 140 is typically an electrogram. The display device 162 then displays on a screen a representation of the ultrasound image and/or a representation of the electrogram, which can be seen in more detail with reference to FIG. 6 discussed below.

The electronic tool 100 may also include a printer 158 to produce a paper copy of the display. The printer 158 receives the data signal for the paper copy through line 160. An input device 148 may also be included with the electronic tool 100. The input device 148 may include one or more various input interfaces, such as a keyboard, mouse, or stylus. The input device 148 communicates with the processor 146 through line 150.

Figure 2:
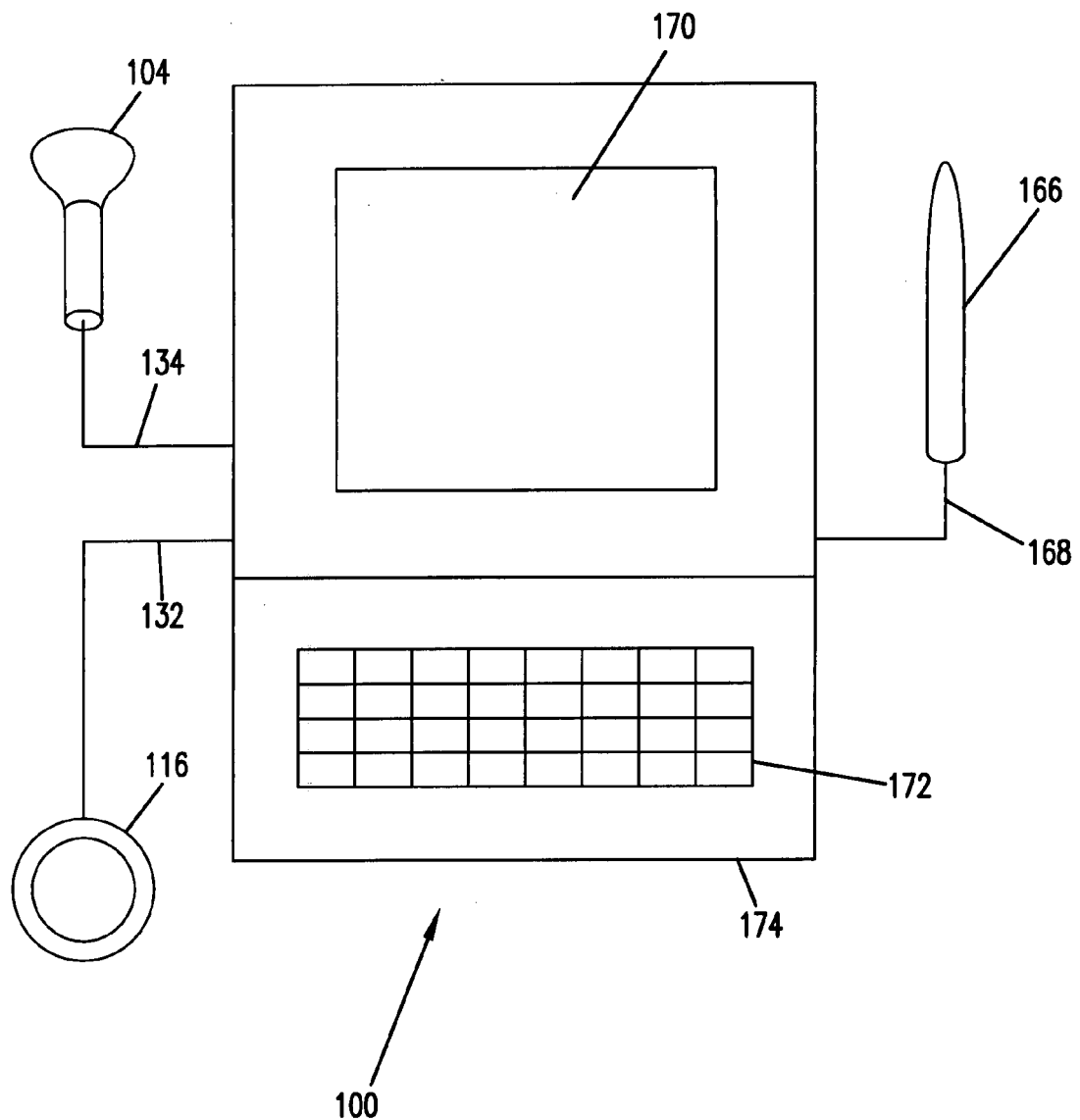
FIG. 2 shows an exterior of an electronic tool according to a preferred embodiment incorporating a display screen, keyboard, and stylus.

FIG. 2 shows an external view of the electronic tool 100 according to a preferred embodiment of the present invention. The tool 100 includes the external transducer 104 for sending and receiving ultrasound energy used for creating images. The tool 100 also includes an antenna 116 for sending and receiving modulated electromagnetic signals that may establish bi-directional communications with the implantable device 122. The tool 100 that is shown includes an input device 148 (see FIG. 1.) having both a keyboard 172 and a stylus 166 that allow the user to input information such as function selections. The stylus 166 communicates with the input device module 148 through line 168.

The electronic tool 100 also includes a display screen 170 controlled by the display device 162. The display screen 170 may be a liquid crystal display (LCD) or other display type such as a cathode ray tube (CRT). The display screen 170 may show various forms of information, such as programmer menus, device parameter settings, the image generated by the image device 136, and any information sent or received by the communications device 140.

The electronic tool 100 may be enclosed within a housing 174 made of metal, plastic, or other rigid material. The keyboard 172 and display screen 170 may be integrated into the housing 174 such that the electronic tool is enclosed within a single housing. Alternatively, multiple housings may be provided for various components, such as including a first housing for the display screen 170, a second housing for the keyboard 174, a third housing for the processor 146, a fourth housing for communications device 140, and a fifth housing for the imaging device 136.

Figure 3:
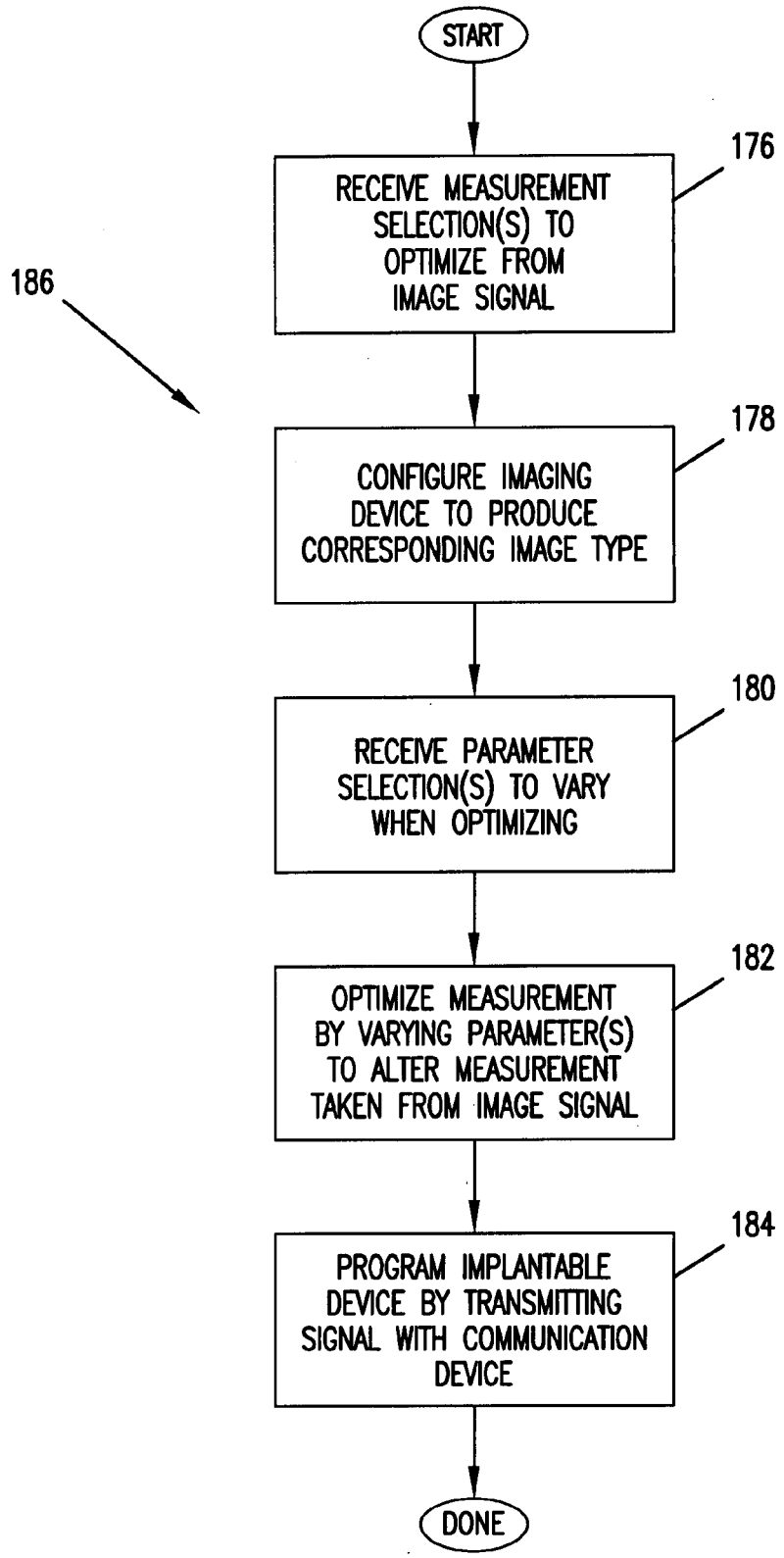
FIG. 3 depicts an exemplary operational flow of the processing steps of one embodiment of the present invention.

FIG. 3 shows the operational flow 186 of the processing steps of one embodiment whereby the operation of the heart stimulation device 122 is optimized. The process begins by the processor 146 receiving an input selection from a user at selection operation 176. The display screen 170 may provide a user interface that allows the user to make selections from menus. A measurement menu may be provided to display the response measurements that the user can select to optimize. These may include but are not limited to ejection fraction, stroke volume, end diastolic volume, E/A (early wave/atrial kick) separation, cardiac output, and wall synchronization of the septum-lateral wall displacement. Using an input device 148, the user then selects the desired measurement(s) to optimize.

After receiving the measurement selection(s), the processor 146 then configures the imaging device 136 to produce an image type that corresponds to the selected measurement(s) at configure operation 178. For example, if cardiac output or stroke volume is desired, the processor 146 may configure the imaging device 136 to produce an aortic flow image rather than an ordinary image of the heart. The operator then places the transducer 104 over the aorta. If volume and ejection fraction measurements are desired, the processor 146 may configure the imaging device 136 to produce a ventricular cross-section image, and the operator places the transducer 104 over the ventricle. If a filling profile measurement is desired, the processor 146 may configure the imaging device 136 to produce a mitral flow image, and the operator places the transducer 104 over the mitral valve.

Once the imaging device 136 has been properly configured, the processor 146 may then receive a selection from the user from a menu of device parameters that may be varied to alter the chosen measurement. The parameters may include but are not limited to the atrial-ventricular (A/V) delay, the lower rate limit, the sensed A/V offset, the maximum sensor rate, the maximum tracking rate, and the right ventricle-left ventricle delay. For certain parameters, processor 146 may accept ranges entered by the user, such as an upper and lower limit to the atrial-ventricular (A/V) delay. By this point, the imaging device 136 may be providing the appropriate image signal to the processor 146, which then extracts the measurement(s) from the image signal and displays the measurement(s) on the display screen 170. A representation of the image signal itself may also be displayed so the operator may visualize the response of the heart.

After the desired parameter and corresponding range have been entered, the processor 146 begins to optimize the measurement(s) at optimize operation 182 by varying the chosen parameter within the range by communicating instructions to the heart stimulation device 122. The optimization process is discussed in more detail below with reference to FIG. 4. Once the measurement(s) taken from the image signal reaches the optimum value, the optimization process terminates and the current value of the parameter(s) is taken to be the optimal value for the chosen measurement (s). The processor 146 may make other measurements at this operation as well, such as those to be stored by the tool 100 or the heart stimulation device 122 for trending purposes including measurements such as heart size that cannot be altered through device parameter manipulation.

The processor 146 then programs the heart stimulation device 122 with the optimal value(s) for the parameter(s) at program operation 184. The processor passes the programming instruction including the parameter(s) and optimal value(s) to the heart stimulation device 122 through a telemetered signal provided by the communications device 140. The program operation 184 may also involve the processor 146 sending a programming instruction including a measurement, such as the previously selected measurement or another, that is to be stored in the memory 124 of the processing device so that it can be retrieved by the electronic tool 100 at a later date for trending purposes.

As discussed above, FIG. 4 shows the optimization step 182 in greater detail. The optimization step 182 begins by the processor 146 receiving the image signal taken from the imaging device 136 at image operation 188. At this point, the processor 146 may also be streaming the image signal to the display device 162 for display on the display screen 170, or the image device 136 may provide the image signal to the display device 162 directly.

The processor 146 then processes the data of the image signal at process operation 190 to make the selected measurement(s) by using image processing techniques known in the art. For example, the processor 146 may measure the velocity from the aortic flow image and integrate the velocity with respect to time when determining cardiac output. In another example, to measure lateral wall displacement, the processor 146 may detect and measure motion of an echogenic lead located on the lateral wall. Once the measurement(s) are obtained, the measured value(s) are compared to an optimum value(s) at compare operation 192. In the lateral wall displacement example, the optimum value may be a threshold displacement that must be reached or exceeded to be optimal. The optimum value for each measurement may be one that is stored in memory 152 of the tool 100 or one that is specified by the user when selecting the tool at selection operation 176 of FIG. 3.

After the comparison has occurred, query operation 194 detects whether the measurement(s) equal the optimum value(s), or exceeds it in the case of some measurements such as lateral wall displacement. If so, then the optimization operation 182 reaches stop operation 198 and operation proceeds to program operation 184 of FIG. 3. If query operation 194 detects that the measurement(s) are not equal to the optimum value(s) or is some cases whether the measurement is less than the optimum value, then parameter operation 196 triggers the processor 146 to generate an instruction that alters the parameter value(s) within the heart stimulation device 122 by sending the instruction through a signal provided by communications device 140.

After allowing for the heart stimulation device 122 to implement the new parameter value(s) and allowing the patient's heart 102 to respond to the change, receive operation 188 again retrieves an image signal containing the data showing the heart's response to the change. The optimization process 182 then repeats continuously until the measurement(s) equal the optimum value(s). Finding that the measurement(s) do equal, or is some cases exceeds, the optimum value(s) may require determining whether the measurement(s) lie within a permissible tolerance range centered about the optimum value(s).

Figure 5:
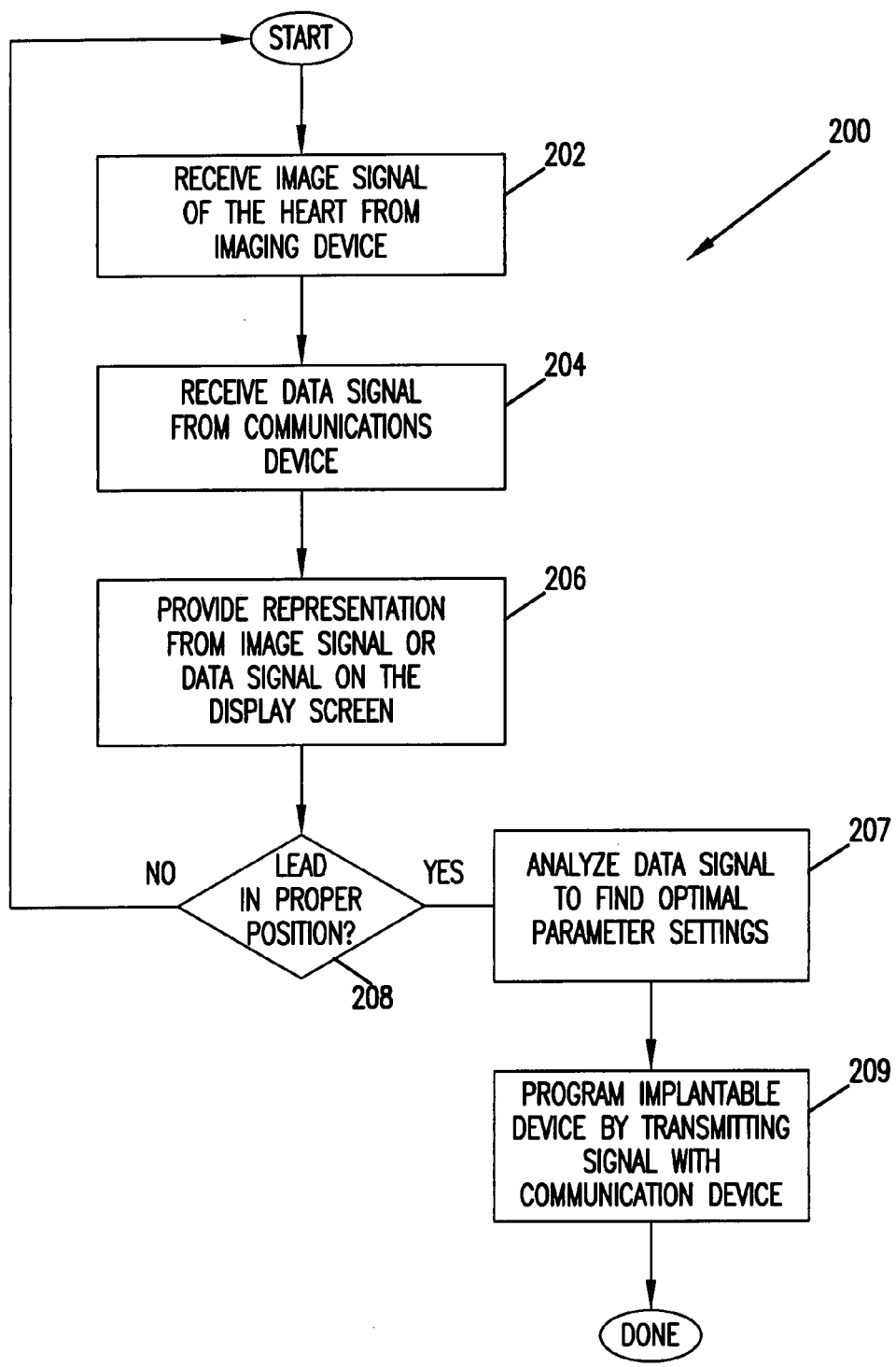
FIG. 5 illustrates an exemplary operational flow of another preferred embodiment.

FIG. 5 shows another process that may be implemented using the tool 100. This process 200 involves placing leads of the heart stimulation device 122 within the heart 102 of the patient. This process 200 begins by the processor 146 retrieving the image signal from the imaging device 136 at image operation 202. For determining lead placement, the image signal will typically be an actual picture of the heart 102. The processor 146 retrieves a data signal from the communications device 140 at data operation 204. The data signal may be an intracardiac electrogram signal, a pacing impedance signal, or other device/lead parameter signals that are useful in optimizing the lead position.

At representation operation 206, a representation of the image signal (i.e., an actual picture of the heart) is displayed on the display screen 170, which also displays a representation of the data signal (i.e., an electrogram, etc.). Displaying both the representation of the image signal and the representation of the data signal permits the user to see both the electrical and mechanical responses of the heart 102 and permits the delay between the two to be observed. The process continues to query operation 208, which detects whether the lead is in a proper position. The query operation 208 may function by prompting the user to indicate through the input device 148 that the lead has reached a proper location. Alternatively, the processor 146 may analyze the data signal to determine whether the lead has a proper location based on various measurements of heart activity. If no indication of proper location is detected, operation returns to receive operation 202 where the procedure is repeated.

Once query operation 208 finds that the lead is in a proper location, the processor 146 analyzes the data signal to find optimal parameter settings at analyze operation 207. For example, the processor 146 may determine the natural A/V delay from the data signal by using the lead as a sensor to detect intrinsic heart activity. From this analysis, the processor 146 can determine optimal parameter settings. After completing the analysis, the processor 146 formulates an instruction including the optimal parameter settings that are then transmitted to the heart stimulation device 122 with the communications device 140 at program operation 209.

Figure 6:
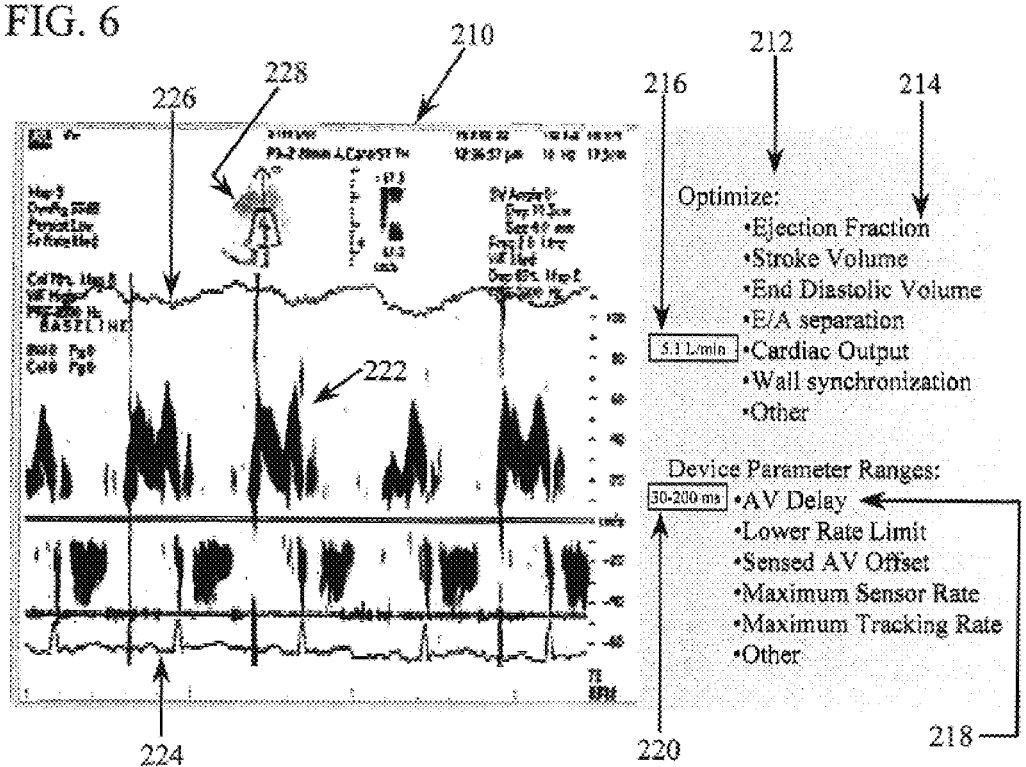
FIG. 6 illustrates an exemplary screen display provided by one embodiment.
Figure 6:
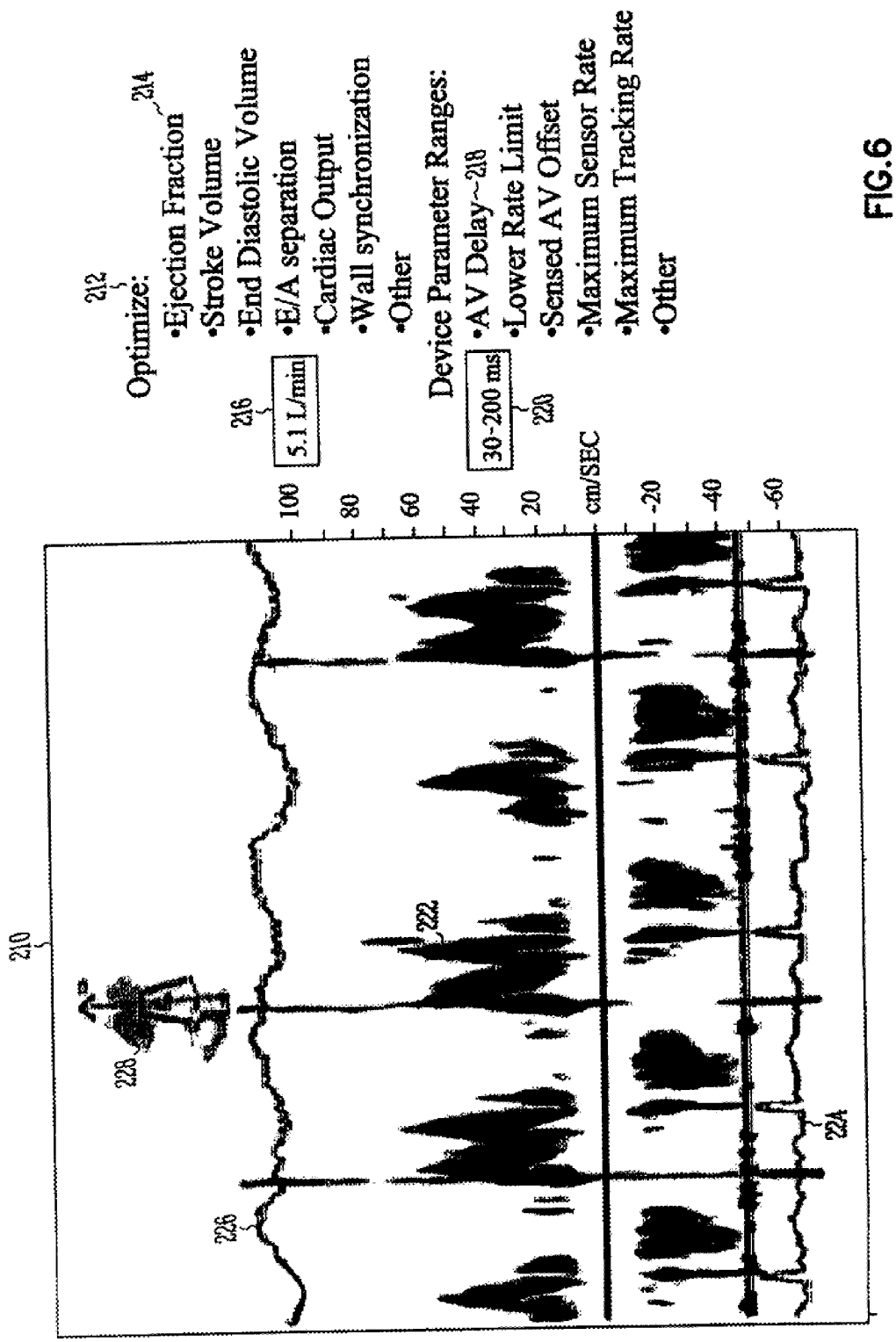

FIG. 6 shows an example of the contents 210 of display screen 170 of the electronic tool 100. The contents 210 of this embodiment include a menu area 212 that includes measurement selections 214 and parameter selections 218. Also, measurement area 216 is included to show the current measurement value, and parameter area 220 is included to receive and show the current parameter range. As shown, the selected measurement is cardiac output and it has a current measured value of 5.1 liters per minute. The selected parameter is A/V delay and the designated range is from 30 to 200 milliseconds The contents 210 of the screen 170 also include an image area 222 for displaying a representation of the image signal, such as displaying an actual picture of the heart or an image of flow. As shown, an image of flow through the mitral valve is being displayed in the image area 222. The display may also include an external cardiac signal area 224 for displaying a representation of a data signal, such as an external or surface electrocardiogram. The external electrocardiogram signal may originate from an EKG machine that feeds an output signal into an analog input port forming part of input device 148 (See FIG. 1). The analog input port may then direct the output signal to the display device 162. Alternatively, the EKG functionality could be included as part of the functionality of the tool 100.

The contents 210 of the display screen 170 also include an intracardiac signal area 226. This area is for displaying a representation, such as an intracardiac electrogram, of a data signal received by the communications device 140 from the heart stimulation device 122. Supplemental image area 228 is also included in the display screen 170 to show an actual but limited image of image of the heart to indicate to the user where the transducer 104 is located relative to the heart 102. The supplemental image area 228 is useful when a flow image is to be used and the user must position the transducer 104 over the aorta or a particular valve where flow is to be measured.

Figure 4:
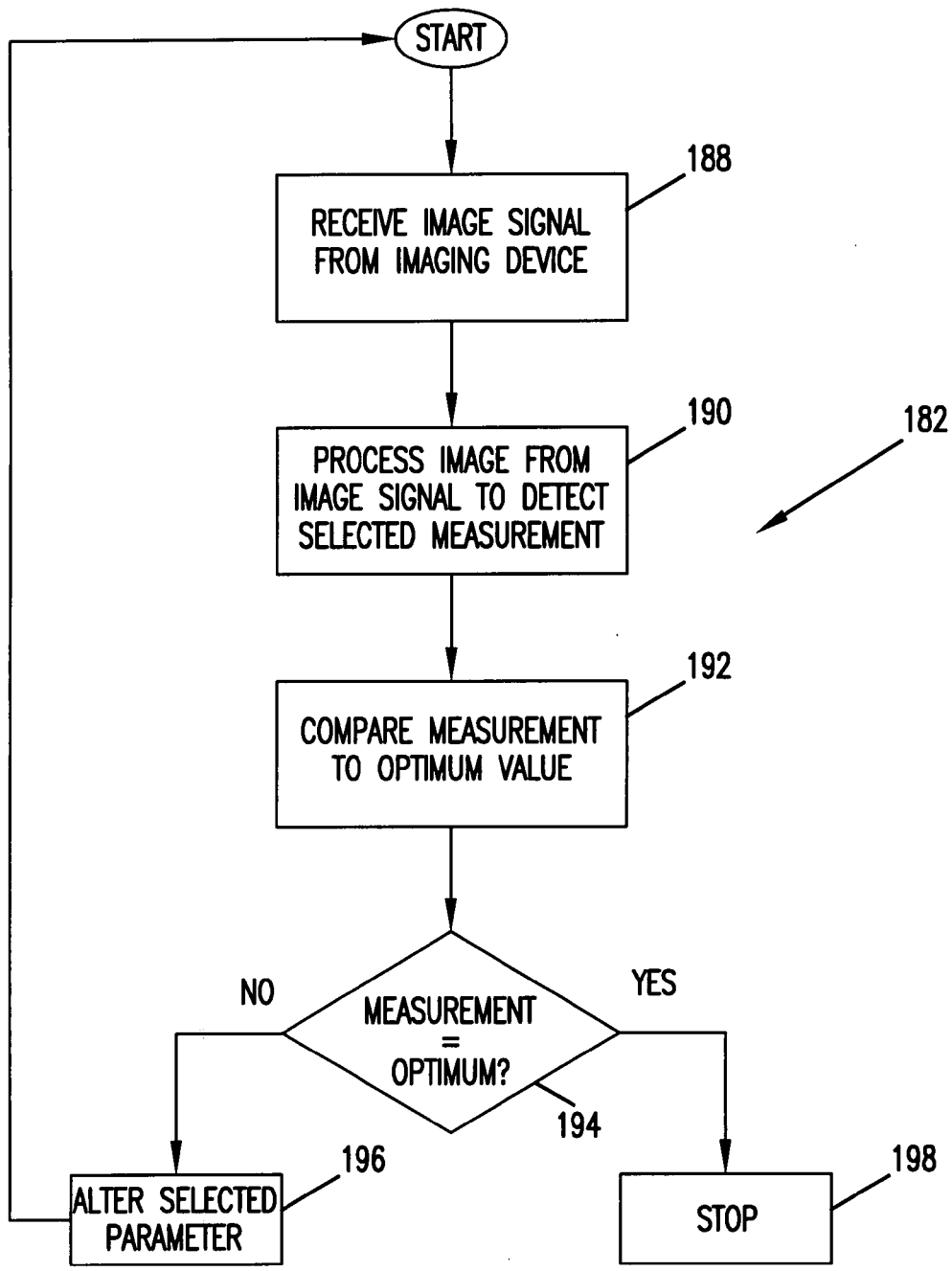
FIG. 4 shows an exemplary operational flow of an optimization step of the embodiment of FIG. 3.

The embodiments of the operations of the invention, such as but not limited to those of FIGS. 3, 4, and 5 are implemented as logical operations in the system. The logical operations are implemented (1) as a sequence of computer implemented steps running on a computer system of the electronic tool comprising a processing module such as processor 146 and/or (2) as interconnected machine modules running within the computing system.

This implementation is a matter of choice dependent on the performance requirements of the computing system implementing the invention. Accordingly, the logical operations making up the embodiments of the invention described herein are referred to as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

While the invention has been particularly shown and described with reference to preferred embodiments thereof, it will be understood by those skilled in the art that various other changes in the form and details may be made therein without departing from the spirit and scope of the invention.

What is claimed is:

1. A method of programming a heart stimulation device of a patient, the method comprising the steps of:
   generating, with an imaging device, an image signal representative of an image of an area around the heart;
   receiving a first signal transmitted by the heart stimulation device;
   analyzing, with a processing device in electrical communication with the imaging device and a communications device, the first signal to measure a response of the heart; and
   producing, with the processing device and in response to the measured response, a second signal encoding instructions for varying one or more stimulation parameters of the heart stimulation device.

2. The method of claim 1, further comprising a step of communicating the second signal to the heart stimulation device.

3. The method of claim 1, further comprising a step of displaying a representation of the image signal and a representation of the first signal on a display screen.

4. The method of claim 1, further comprising a step of positioning leads of the heart stimulation device within the heart, wherein the image signal and the response extracted from the first signal indicate the position of the leads, and wherein the instructions encoded by the second signal are based upon the position of the leads.

5. The method of claim 1, comprising altering an atrial-ventricle delay using information generated with the imaging device.

6. The method of claim 1, comprising altering a right ventricle-left ventricle delay using information generated with the imaging device.

7. The method of claim 1, comprising altering a synchronization of a septum-lateral wall displacement using information generated with the imaging device.

8. The method of claim 1, comprising measuring an aortic flow from the image signal.

9. The method of claim 1, comprising measuring a ejection fraction from the image signal.

10. The method of claim 1, comprising measuring a size of the heart of the patient from the image signal.

11. An electronic tool for communicating with an implantable heart electrostimulation device and for imaging a chest region of a patient, the electronic tool comprising:
    an imaging device that radiates energy onto the chest region and that detects energy reflected by the chest region to produce an image signal;
    a communication device that receives a first signal with encoded information from the heart electrostimulation device; and
    at least one processor in electrical communication with the imaging device and the communication device, wherein the at least one processor formulates an instruction for the heart electrostimulation device by analyzing the image signal or by analyzing the information encoded on the first signal.

12. The electronic tool of claim 11, further comprising:
    a display screen that is communicatively linked to the imaging device and that displays a representation of the image signal or a representation of the encoded signals.

13. The electronic tool of claim 11, wherein the processor communicates with the imaging device, analyzes the image signal, and formulates a first signal that is sent to the heart electrostimulation device.

14. The electronic tool of claim 11, wherein the encoded signals include a first signal that is received from the heart stimulation device by the communication device, the processor that communicates with the communication device is configured to analyze the first signal and to formulate a second signal, wherein the communication device sends the second signal to the heart electrostimulation device.

15. The electronic tool of claim 11, further comprising:
at least one display screen in electrical communication with the imaging device and the communication device, wherein the at least one display screen includes a display of a representation of the image signal or a display of information from the first signal sent from or received by the communication device.

16. The electronic tool of claim 11, wherein the first signal is sent by the communications device, the electronic tool further comprising:
an input device configured for receiving input information from a user, wherein the at least one processor analyzes the information received by the input device to formulate the information encoded on the first signal.

17. The electronic tool of claim 11, wherein the imaging device comprises an ultrasound transducer array that radiates and receives ultrasound energy.

18. The electronic tool of claim 11, wherein the communications device comprises a wire loop that radiates and receives magnetic signals.

19. The electronic tool of claim 11, wherein the communications device includes an RF antenna that transmits and receives RF signals.

20. The electronic tool of claim 11, wherein the heart electrostimulation device has electrical leads located in the patient's chest area that reflect energy radiated by the imaging device and wherein the imaging device detects the energy reflected by the electrical leads to produce an image signal that causes the electrical leads to appear on the display screen.

21. The electronic tool of claim 11, wherein the processor formulates the instruction such that the instruction is configured to alter an atrial-ventricle delay.

22. The electronic tool of claim 11, wherein the processor formulates the instruction such that the instruction is configured to alter a right ventricle-left ventricle delay.

23. The electronic tool of claim 11, wherein the processor formulates the instruction such that the instruction is configured to alter a synchronization of a septum-lateral wall displacement.

24. The electronic tool of claim 11, wherein the processor is adapted to measure an aortic flow from the image signal.

25. The electronic tool of claim 11, wherein the processor is adapted to measure an ejection fraction from the image signal.

26. The electronic tool of claim 11, wherein the processor is adapted to measure a size of the heart of the patient from the image signal.

27. The electronic tool of claim 11, wherein the instruction comprises a value measured by the processor for storage by the heart electrostimulation device.

28. An electronic tool for communicating with an implantable heart electrostimulation device and for imaging a chest region of a patient, the electronic tool comprising:
means for generating an image of the chest region;
means for formulating an instruction for the heart electrostimulation device by analyzing the image; and
means for transmitting information including the instruction to the heart electrostimulation device.

29. The electronic tool of claim 28, wherein the means for generating an image comprises a display screen for providing a representation of an image signal to a user and an input device for receiving information input by a user that is encoded onto a first signal transmitted to the heart electrostimulation device.

30. The electronic tool of claim 28, wherein the means for transmitting information transmits encoded information as an RF signal.

31. The electronic tool of claim 28, wherein the means for transmitting information comprises a means for bi-directional communication of RF signals.

* * * * *

UNITED STATES PATENT AND TRADEMARK OFFICE
CERTIFICATE OF CORRECTION

PATENT NO. : 7,286,877 B2
APPLICATION NO. : 10/792562
DATED : October 23, 2007
INVENTOR(S) : Douglas Daum It is certified that error appears in the above-identified patent and that said Letters Patent is hereby corrected as shown below:

Delete drawings sheet 6-6 and substitute therefor the drawing sheets, consisting of fig. 6 as shown on the attached page.

Signed and Sealed this

Twenty-seventh Day of May, 2008

JON W. DUDAS
*Director of the United States Patent and Trademark Office*